(12) United States Patent
Helgesson (10) Patent No.: US 8,714,032 B2
(45) Date of Patent: May 6, 2014

(54) UNIVERSAL FORCE MEASUREMENT APPARATUS AND METHOD

(76) Inventor: Marcus Gustaf Helgesson, Danderyd (SE)

( * ) Notice: Subject to any disclaimer, the term of this patent is extended or adjusted under 35 U.S.C. 154(b) by 155 days.

(21) Appl. No.: 13/474,732

(22) Filed: May 18, 2012

(65) Prior Publication Data

US 2013/0305841 A1 Nov. 21, 2013

(51) Int. Cl.
*G01D 7/00* (2006.01)
*G01L 1/22* (2006.01)

(52) U.S. Cl.
USPC .................. 73/862.043; 73/862.041

(58) Field of Classification Search
USPC ...................... 73/862.041–862.045
See application file for complete search history.

(56) References Cited

U.S. PATENT DOCUMENTS

| 2009/0293586 A1 | 12/2009 | Schleif et al. |
| 2009/0320556 A1 | 12/2009 | Collins et al. |
| 2011/0067494 A1* | 3/2011 | Tezuka et al. .................... 73/471 |
| 2013/0298633 A1* | 11/2013 | White et al. ..................... 73/1.15 |
| 2013/0327161 A1* | 12/2013 | Israelachvili .............. 73/864.91 |

FOREIGN PATENT DOCUMENTS

SE 527714 C2 5/2006

* cited by examiner

*Primary Examiner* — Lisa Caputo
*Assistant Examiner* — Jonathan Dunlap (57) ABSTRACT

A universal force measurement apparatus has a top plate onto which a first test object is mounted. The top plate is connected to a middle plate via a sliding member, for example a linear ball slide having a one dimensional degree of freedom. A first load cell is connected to the top plate and the middle plate, hereby preventing them from moving relative to one another in the direction of the degree of freedom of the sliding member. The mid plate is then connected to a second load cell which registers forces in the vertical direction. The second load cell is also connected to a base plate which is placed on a rigid surface. Forces from another object or media acting on the first test object will now be registered by the first and second load cells in the horizontal and vertical directions.

20 Claims, 4 Drawing Sheets

UNIVERSAL FORCE MEASUREMENT APPARATUS AND METHOD

TECHNICAL FIELD

The present embodiments generally relate to an universal force measurement apparatus and method for force measurements.

BACKGROUND

In many engineering, product development and research applications there is often a need to measure and study physical properties of components, objects and materials to better understand how the properties can be optimized for a specific purpose in a specific environment. Such physical properties are for example surface properties, adhesive properties, abrasive properties, impact properties and aerodynamic properties. A common characteristic among all the various fields/applications is that the properties are linked to one or several forces interacting between the components/objects/materials.

Measurements to study interacting forces between components/objects/materials are often made using very sophisticated and expensive types of apparatuses; for example pin-on-disc machines, friction testers, adhesion testers, wear testers, tensile testing machines, impact testers and wind tunnels. For example, US 2009/0293586 discloses a device for measuring coefficients of friction, SE 527 714 C2 discloses an apparatus and method to study frictional properties between two test objects and US 2009/0320556 discloses a monitoring apparatus for measuring the dynamic coefficient of friction of a surface.

A growing field within product development and research is to use computer aided engineering software and methods to simulate components or mechanisms and study their behavior in a virtual environment before physical prototypes are made or to try to minimize the need of using physical prototypes since physical prototypes often are time consuming and expensive. A major challenge when using simulations in product development is to ensure that material properties and physical interaction parameters, which directly affect the outcome of the simulation (for example in finite element analysis and multi body simulations), are correct. In this aspect there is still room for improvement since in most cases it is not sufficient to look up tabulated generic data for a material or physical interaction parameter and directly apply this to a specific computer model which is a very common approach today.

More and more products rely on the interaction between the product and the person using it, for example tablet PCs operated by the human touch. It is valuable to objectively be able to measure and quantify what a material or geometry feels like for anyone developing and selling these types of products ranging all the way from tablet PCs to clothing/textiles. However, up until today, to measure and quantify the sense of touch and the perceptive characteristics of a material/geometry has been very difficult to do.

Therefore, there is room for improvement and to provide a force measurement apparatus and method capable of being applied to a wide range of physical events/phenomena where there is a need to measure forces (both static and dynamic, such as sliding or rolling, forces) between two objects which is universal, mobile and easy to apply. The apparatus and method should also have the capability to study the contact forces between human skin and a material/object.

SUMMARY

It is a general objective to provide a force measurement apparatus and method capable of studying forces that are created due to the physical interaction between two bodies in mainly two dimensions.

The above and other objects are met by embodiments disclosed herein.

An aspect of the embodiments relates to a force measurement apparatus or device configured to study reaction forces in a horizontal direction and a vertical direction between a first test object and a second test object. The force measurement apparatus comprises a rigid top plate onto which the first test object is configured to be mounted or fixated, a rigid middle plate and a rigid base plate configured to be positioned on a rigid surface.

A sliding member with a translational degree of freedom mechanically connects the middle plate to one of the top plate and the base plate, preferably the top plate. The sliding member is configured to allow the middle plate and the one of the top plate and the base plate, preferably the top plate, to move relative to one another in a direction of the translational degree of freedom of the sliding member. A first load cell is connected to the middle plate and to the one of the top plate and the base plate, preferably the top plate, in such a way that a relative motion between the middle plate and the one of the top plate and the base plate, preferably the top plate, in the translational degree of freedom of the sliding member is inhibited, prevented or prohibited. The first load cell is configured to register horizontal forces acting on the first test object when the second test object is brought to physically interact with the first test object. These horizontal forces are oriented in the direction of the translational degree of freedom of the sliding member. The first load cell is configured to output a first output signal representative of the horizontal forces. The force measurement apparatus further comprises a second load cell connected to the middle plate and the other of the top plate and the base plate, preferably the base plate. The second load cell is configured to register vertical forces in a vertical direction on the first test object when the second test object is brought to physically interact with the first test object. The second load cell is configured to output a second output signal representative of the vertical forces.

Another aspect of the embodiments relates to a method to study reaction forces between a first test object and a second test object. The method comprises fixating the first test object to a rigid top plate of a force measurement apparatus as defined above. A second test object is brought to physically interact with the first test object. Horizontal forces acting on the first test object are registered by a first load cell of the force measurement apparatus. The method further comprises generating a first output signal representative of the horizontal forces acting on the first test object by the first load cell. Vertical forces acting on the first test object is registered by a second load cell of the force measurement apparatus. The method also comprises generating a second output signal representative of the vertical forces acting on the first test object by the second load cell.

In a particular embodiment, the method to study reaction forces between a first test object and a second test object comprises fixating the first test object to a rigid top plate movable relative to a rigid middle plate in a direction of a translational degree of freedom of a sliding member mechanically connecting the top plate to the middle plate. A second test object is brought to physically interact with the first test object. Horizontal forces acting on the first test object are registered by a first load cell connected to the top plate and to the middle plate in such a way that a relative motion between the top plate and the middle plate in the translational degree of freedom of the sliding member is prohibited. The method further comprises generating a first output signal representative of the horizontal forces acting on the first test object by the first load cell. Vertical forces acting on the first test object is registered by a second load cell connected to the middle plate and to a base plate configured to be positioned on a rigid surface. The method also comprises generating a second output signal representative of the vertical forces acting on the first test object by the second load cell.

In an embodiment, the sliding member has a low coefficient of friction.

In an embodiment, the sliding member comprises a linear ball slide or a plurality of linear ball slides.

In an embodiment, a connection between the first load cell, the top plate and the middle plate comprises a counter bore with a through-hole made in the top plate. A first screw is positioned in the counter bore and the through-hole made in the top plate. A first hollow spacer is positioned around a portion of the first screw protruding from underneath the top plate. In an embodiment, a first joint, such as a first right angle ball and socket joint, is connected via a thread and threaded rod to a first side of the first load cell. The first right angle ball and socket joint is positioned around a portion of the first screw where the first hollow spacer ends. A bolt preferably connects the first right angle ball and socket joint, the first hollow spacer and the first screw. A second joint, such as a second ball and socket joint, preferably a second right angle ball and socket joint, is preferably connected via a thread and threaded rod to the other side of the first load cell with a second hollow spacer positioned in between the second ball and socket joint and the middle plate. A second screw is inserted in a threaded hole in the middle plate joining together the second right angle ball and socket joint and the second hollow spacer.

In an embodiment, the force measurement apparatus comprises an analog to digital converter connected to the first load cell and the second load cell. The analog to digital converter is preferably powered by a low voltage output from a computer. The analog to digital converter is advantageously configured to provide an excitation voltage to the first load cell and the second load cell. In a particular embodiment, the analog to digital converter is configured to convert the first output signal to a first digital output signal and the second output signal to a second digital output signal and to forward the first digital output signal and the second output signal to a computer configured to present the first digital output signal and the second digital output signal in real time and/or to store the first digital output signal and the second digital output signal to a file in a computer program run by the computer. The computer program run on the computer is preferably configured to process the first digital output signal to compensate for an internal coefficient of friction or internal friction in the sliding member in the horizontal force represented by the first digital output signal.

In an embodiment, the force measurement apparatus comprises an external display comprising a Liquid Crystal Display (LCD) and/or a Light-Emitting Diode (LED) dot matrix display. The external display is connected to the first load cell and to the second load cell.

In an embodiment, the force measurement apparatus further comprises a ground cable connected to a metallic part of the force measurement apparatus.

In an embodiment, the first load cell is a s-type load cell and the second load cell is a single point load cell.

In an embodiment, the second test object is a hand held test object.

In an embodiment, the second test object is a media comprising a liquid and/or a gas.

In an embodiment, the force measurement apparatus is portable and therefore mobile.

In an embodiment, the sliding member has two translational degrees of freedom. In such a case, the force measurement apparatus preferably comprises a third load cell connected to the top plate and to the middle plate in such a way that in a second translational degree of freedom of the sliding member is prohibited. The third load cell is configured to register horizontal forces acting on the first test object when the second test object is brought to physically interact with the first test object. These horizontal forces registered by the third load cells are oriented in a direction of the second translational degree of freedom of the sliding member.

In an embodiment, the second load cell is configured to register the vertical forces regardless of where the vertical forces are acting on the first test object.

In an embodiment, the top plate, the middle plate and the base plate each comprises counter bores with through-holes into which screws are inserted to connect the top plate and the middle plate to the sliding member, connect the first load cell to the top plate and the middle plate and connect the second load cell to the base plate and to the middle plate.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

In a particular embodiment, a force measurement apparatus comprises a top plate (also referred to as the mounting plate) onto which a first test object can be mounted, a middle plate and a base plate. Furthermore, a sliding member with a low static coefficient of friction, preferably below 0.2, having at least one degree of freedom is installed and positioned in between the top plate and the middle plate. A horizontally oriented load cell (also referred to as the first load cell) is connected to the top plate and to the middle plate and a vertically oriented load cell (also referred to as the second load cell) is connected to the middle plate and to the base plate.

By means of connecting the horizontal load cell with its load detecting axis oriented in the same direction as the degree of freedom of the sliding member to both the top plate and the middle plate, relative motion in the degree of freedom of the sliding member between the top plate and the middle plate is prevented. Therefore, any reaction forces on the top plate directed in the load detecting axis of the horizontal load cell will be detected by the horizontal load cell.

The vertically oriented load cell is capable of detecting forces oriented in the vertical direction no matter where the vertical forces are acting on the top plate. Hereby the two load cells will register both horizontally and vertically oriented forces simultaneously for any reaction force acting on an object/test specimen mounted on or fixated to the top plate.

Figure 4:
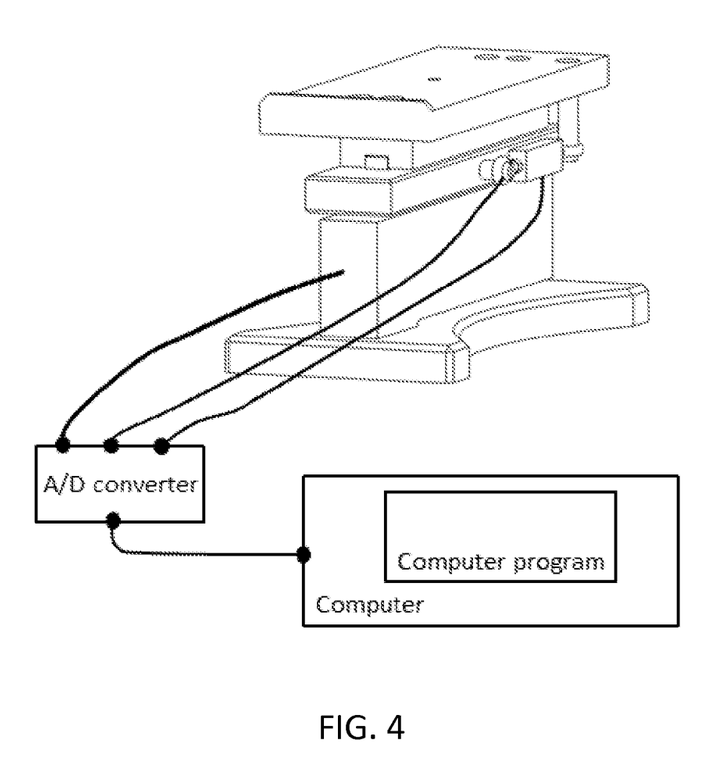
FIG. 4 Illustrates the force measurement apparatus connected to an analog to digital converter (ND converter) which is connected to a computer where a computer program is used to present and save the force data from the load cells.

The horizontal and vertical load cells are preferably connected to an analog to digital converter (also referred to as an ND converter), or a respective A/D converter, capable of receiving and amplifying the millivolt signals from the load cells and transforming the analog signal to a digital counterpart, see FIG. 4. The A/D converter will, in a preferred embodiment, also provide the excitation voltage needed for both load cells to operate. The digitized load cell signal from the A/D converter is passed onto a computer where the horizontal and vertical force can be presented and manipulated in a computer program.

Hereby, forces acting on an object/test specimen/material fixated to the top plate can be easily detected and recorded. Hence, the embodiments provide an apparatus and a method applicable to a wide range of physical events where forces between objects or materials need to be studied. The apparatus and method can even be used to study contact forces between a human and a material, simply by placing a test specimen onto the top plate and sliding a hand or finger over it.

Current test apparatuses on the market are often limited to one specific area of use; through its generic approach towards performing force measurements the embodiments can be used in more or less unlimited sense, for example but not limited to contact force, friction, adhesion, abrasion and impact measurements.

In a particular embodiment, the force measurement apparatus is mobile (in a preferred embodiment its weight is below 10 lbs.). It can easily be used in an educational setting. A lecturer/teacher can bring the apparatus to class and conduct real-time experiences in front of an audience.

Figure 1:
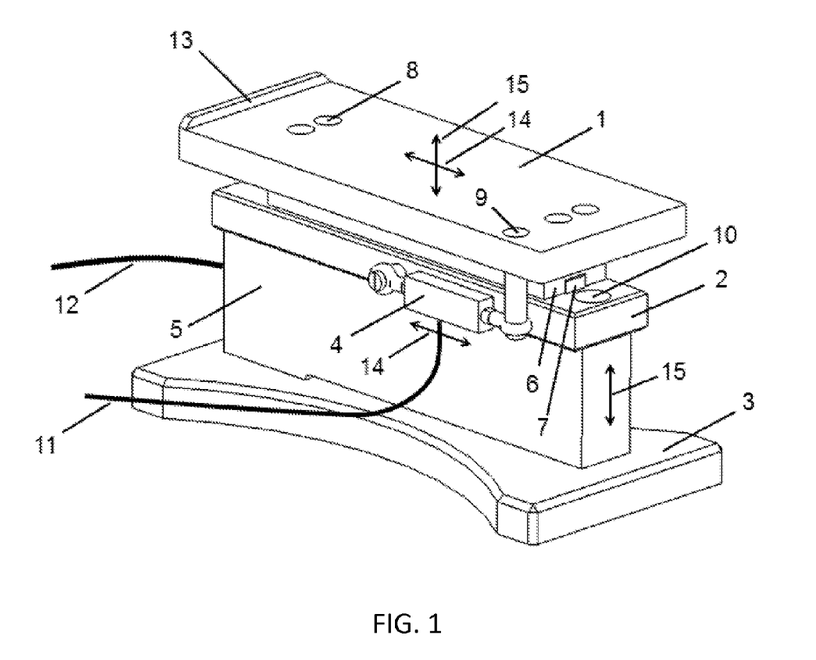
FIG. 1 Illustrates a three dimensional representation of a force measurement apparatus according to an embodiment.

Referring to the drawings, FIG. 1 illustrates an embodiment of the force measurement apparatus in 3D format. When the top plate 1 is subjected to one or several horizontal forces acting in the same direction as the degree of freedom 14 of the sliding member 6, 7 (here represented by a linear ball slide) the vast majority of the horizontal force(s) will translate into the load sensing member referred to as the horizontal load cell 4. When the top plate 1 is subjected to one or several vertical forces acting in the vertical direction 15 the vertical force(s) will translate into the load sensing member referred to as the vertical load cell 5.

The top plate 1 is mounted onto the carrier or carriage 6 of the sliding member using screws positioned in the four counter bores 8 with thru-holes made in the top plate 1. The base 7 of the sliding member is connected to the middle plate 2 using screws inserted into threaded holes in the middle plate.

Before the first load cell 4 is installed, the top plate 1 and middle plate 2 are free to move relative to each other in the degree of freedom 14 of the sliding member 6, 7. When the first load cell 4 (also referred to as the horizontal load cell) is installed and hereby mechanically connecting the top plate 1 to the middle plate 2 the top plate 1 and the middle plate 2 can no longer move relative to one another in the degree of freedom 14 of the sliding member 6, 7. Horizontal forces acting on the top plate 1 in the same direction 14 as the degree of freedom of the sliding member 6, 7 will now translate into the horizontal load cell 4. Hereby, horizontal forces acting on an object mounted on/fixated to the top plate 1 will be detected by the horizontal load cell 4.

A second load cell 5 (also referred to as the vertical load cell) is connected to the middle plate 2 and to the base plate 3. The second load cell 5 will register forces in the vertical direction 15 no matter where the vertical forces are acting on the top plate 1. In FIG. 1 the second load cell 5 is represented by a so called single point load cell. Hereby, vertical forces acting on an object mounted on/fixated to the top plate 1 will be detected by the vertical load cell 5.

Both the horizontal load cell 4 and the vertical load cell 5 have threaded holes in them made upon the time of manufacturing of the load cells and the holes/counter bores in the base plate 3 and middle plate 2 are made so that these holes are aligned with the threaded holes of the vertical load cell 5. In FIG. 1 one of the counter bores 10 made in the middle plate 2 is visible. The counter bores 8 in the top plate 1 are made for screws/fasteners connecting the top plate 1 to threaded holes in the carrier 6 of the sliding member 6, 7 so that the screws or fasteners sit flush with or below the level of the mounting surface of the top plate 1.

Still referring to FIG. 1 the cable 11 connected to the horizontal load cell and the cable 12 connected to the vertical load cell are both connected to an analog to digital converter which amplifies the millivolt signals from the load cells due to the applied load/force in the horizontal and vertical directions and converts them into binary numbers. The analog to digital converter is connected to a computer, preferably to a USB port of the computer using a cable or via a wireless connection. A data acquisition software or computer program is then used to present/display and record force data from the horizontal and vertical load cells 4, 5 to a results file, see FIG. 4. In many applications the quotient horizontal force divided by vertical force or vertical force divided by horizontal force is of interest and these quotients can be presented and saved in the data acquisition software by means of applying a simple mathematical formula to the two load cell signals of the type horizontal load cell value/vertical load cell value, or, vertical load cell value/horizontal load cell value.

An elevated edge 13 can be an integral part of the top plate 1 so that a test object resting on the top plate 1 will not slide off when the test object is subjected to a horizontal force oriented in the degree of freedom 14 of the sliding member 6, 7.

Figure 2:
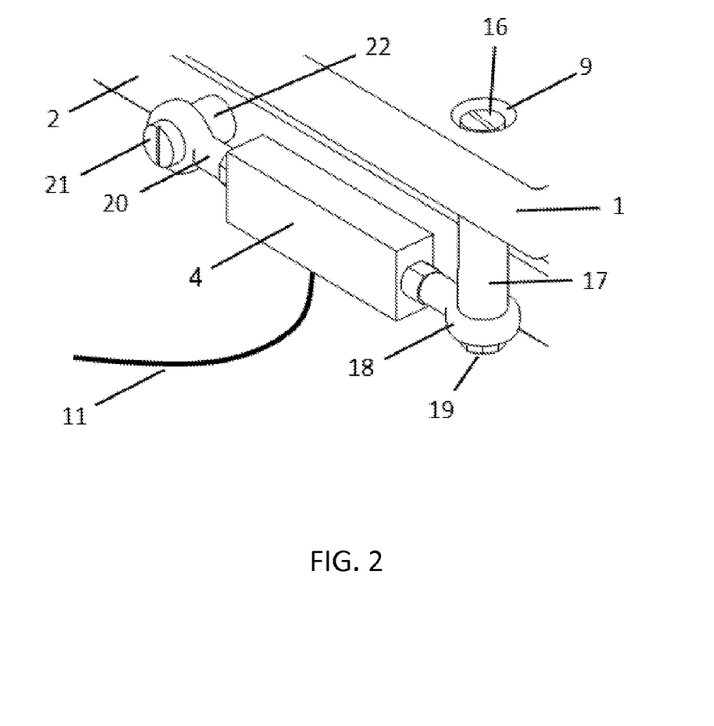
FIG. 2 Illustrates a three dimensional representation of the horizontal load cell and the components linking together the horizontal load cell with the top plate and middle plate.

Now referring to FIG. 2 which is a close up view of the horizontal load cell 4 installation arrangement. A counter bore 9 is made in the top plate 1 into which a screw/fastening member 16 is positioned. A hollow spacer component 17 and a joint 18 are connected to the screw/fastening member securing the hollow component and joint to the top plate 1 using a bolt 19. The joint 18 is connected to a threaded hole in the horizontal load cell 4 using a threaded rod. Yet another joint 20 is connected at the opposite side of the load cell 4 and the joint 20 is connected to the middle plate 2 using a screw 21 and a hollow spacer 22. When the middle plate 2 is manufactured a threaded hole is prepared in the middle plate 2 into which the screw 21 is inserted and fastened.

Figure 3:
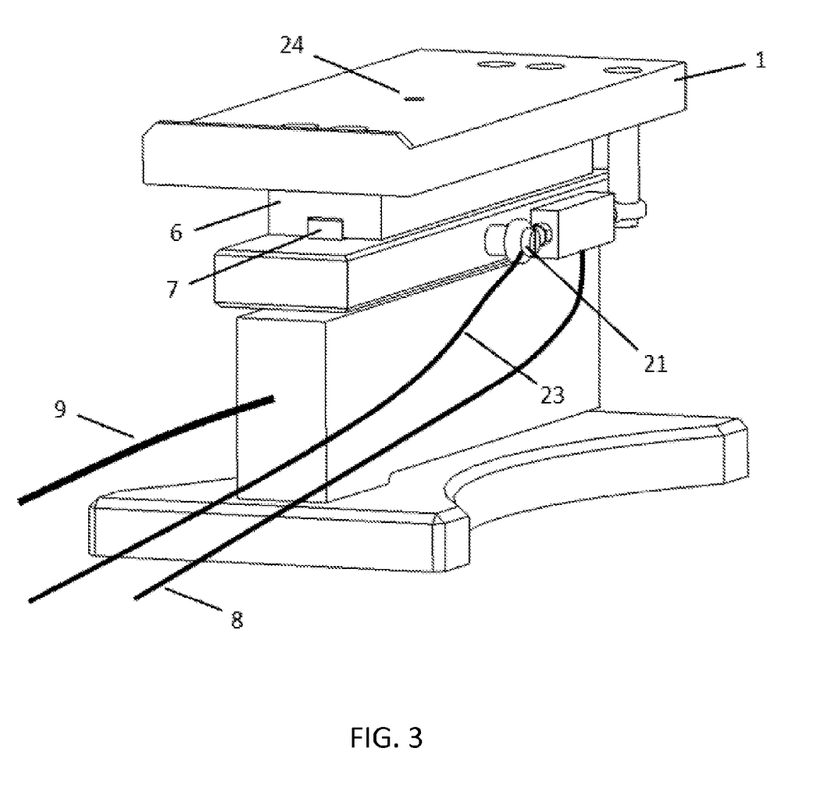
FIG. 3 Illustrates a three dimensional representation of the force measurement apparatus in which a ground cable and a threaded mounting hole made in the top plate are included.

Now referring to FIG. 3 where a ground cable 23 is connected to the metallic screw 21 (the ground cable can be connected to any metal part of the invention if the metal part is in electric connection with any of the load cells) in order to prevent external noise and ground loops in the apparatus. The other end of the ground cable it is preferably connected to a ground terminal in the analog to digital converter commonly referred to as a GND terminal.

Threaded mounting holes can be made in the top plate 1 to allow for easy installation of specific test objects/fixtures. In FIG. 3 a single threaded mounting hole 24 is represented.

Preferably the materials in the top plate 1, middle plate 2 and base plate 3 are of metallic origin, for example aluminum or steel. Polymers or composites can also be used as long as plates 1, 2, 3 are rigid enough.

In a preferred embodiment the analog to digital converter is powered by a low voltage output from the computer, from example a USB port, to which the analog to digital converter is connected and the analog to digital converter then provides the excitation voltage needed to the load cells 4, 5. By making use of this type of power supply no mains voltage or batteries are needed for the force measurement apparatus to operate.

It is possible to add a second horizontal degree of freedom by incorporating a sliding member free to move in two dimensions, or by means of adding a second sliding member with a one dimensional degree of freedom 90 degrees relative to the first sliding member in the horizontal plane. In both cases an additional horizontal load cell or a single bi-axial load cell is be needed to measure forces at 90 degrees angles relative to the first horizontal load cell in the horizontal plane. The added second load cell can be fastened to the top plate 1 and middle plate 2 by using the same type of fastening methods as used for the horizontal load cell 4.

Furthermore, in another arrangement it is possible to mount the top plate 1 onto the vertical load cell 5 which is mounted onto the middle plate 2 which is mounted onto the sliding member 6, 7 which finally is mounted onto the base plate 3. In this special arrangement the horizontal load cell 4 will be mechanically connecting the middle plate 2 to the base plate 3; hereby preventing the middle plate and base plate to move relative to one another in the horizontal direction equal to the directional degree of freedom of the sliding member.

A small amount of a horizontal force acting on the top plate may be lost due to internal friction in the sliding member 6, 7. This small loss can be compensated for by adding a small amount of force to the force value registered by the horizontal load cell 4 in the data acquisition software. The internal friction in the sliding member 6,7 can also be compensated for by adding a value to the quotient between the output signal from the horizontal load cell 4 (or the horizontal force represented by this output signal) and the output signal from the vertical load cell 5 (or the vertical force represented by this output signal).

Since the force measurement apparatus is very generic in the sense that it measures horizontal and vertical reaction forces acting on a first test object connected to the top plate 1, hence also acting on the top plate 1 itself, the force measurement apparatus can be used to study a wide range of physical or mechanical phenomenon, for example but not limited to contact forces, adhesive forces, abrasive forces, impact forces or even aerodynamic forces on a body connected to the top plate 1 when the body is subjected to an air flow. The force measurement apparatus can also be used to study forces interacting between a human hand/finger and a material mounted or connected to the top plate 1 of the force measurement apparatus.

When studying contact forces, adhesive forces, wear forces or colliding/impact forces the first test object which is mounted on or secured to the top plate 1 is preferably planar from a macroscopic perspective. In such a case, the horizontal and vertical components of the forces do not need to be manipulated mathematically due to the geometry of the first test object mounted to the top plate. The second test object can be hand held and have an arbitrary shape. In the case of measuring impact forces the second test object will be dropped or launched onto the first test object which is mounted on or connected to the top plate.

Load cells come in different shapes and formats. It is obvious to anyone skilled in the art that the maximum capacity or range of the load cells can be chosen in such a way that the capacity and range of the load cells are based on the forces that need to be studied. It is also obvious that both the horizontal load cell 4 and the vertical load cell 5 can measure both compression and extension loads/forces, i.e. the load cells are bi-directionally functional, this is also denoted by directions 14, 15 in FIG. 1.

It is also obvious to anyone skilled in the art that the analog to digital converter can have different bit-resolutions which controls the detectable force resolution of the load cells, for example but not limited to 12, 16 or 20 bits. The sampling frequency used when conducting measurements with the force measurement apparatus can range from a few Hz up to several thousands of Hz and beyond depending on what type of phenomenon that is studied.

In FIG. 1-4 the sliding member is represented by a linear ball slide with a carrier and base component. The sliding member can for instance be comprised of a slide table, a pressurized air actuated bearing, a magnetic bearing or multiple ball slides mounted side by side.

The load detecting members in FIG. 1-4 are represented by a so called s-type load cell (the horizontal load cell also referred to as the first load cell 4) and a single point load cell (the vertical load cell also referred to as the second load cell 5) could of course represented by other types of load cells such as beam load cells, cylindrical load cells, donut load cells and similar. The vertical load cell, however, is preferably able to sense the vertical force regardless of where the vertical force is applied to the first test object/top plate 1. In one embodiment strain gauges can be used together with a specific geometry to connect the base plate 3 to the middle plate 2 for which the specific geometry has a known stress vs. strain curve so that the vertical force can be calculated. The same type of reasoning applies to the horizontal load cell 4.

The force measurement apparatus can be used for rotary machine analysis where the rotating machine is mounted on to the top plate or the force measurement apparatus is mounted onto the rotating machinery. Analyzing the registered forces in the frequency domain can for example produce insight into any rotating component misalignment.

The force measurement apparatus can be used to analyze various lubricants and different types of devices connected to the top plate 1, for example but not limited to devices using sliding mechanisms and cogwheels.

Furthermore, the force measurement apparatus can be used or to study the lift force of a helicopter scale model and study the lift capacity at different rotating velocities for different blade configurations. It can be used to study tire forces for a vehicle scale model. If the force measurement apparatus is scaled it can do the same even for a full size ground vehicle. A water tank can be installed onto the top plate and by pulling a ship model inside the water tank the hydrodynamic drag or skin friction can be calculated. The water tank can even have streaming water in it and therefore the ship does not need to move relative to the force measurement apparatus to study hydrodynamic forces.

In the world of sports the force measurement apparatus can be used to study the force components between the blade of a hockey stick and the ice surface similar to that on a hockey rink, for example to optimize a slap shot technique by studying the horizontal and vertical reaction forces during the time the blade of the hockey stick is interacting with the puck and ice surface. The same technique is applicable to a golf shot by means of connecting the peg to the top plate to study how cleanly the ball is hit. The force measurement apparatus can be used to study the traction between a sports shoe and a floor surface by simply placing a piece of the surface onto the top plate 1 and sliding the shoe or a piece of the shoe over it.

Still referring to the world of sports the force measurement apparatus can even be used to optimize the performance of a ski or any other equipment used to transport a person over ice or snow. For example, different waxes can be evaluated either by using the force measurement apparatus in a laboratory setting or by means of placing the force measurement apparatus it in a ski track with snow or ice on it so that it registers the ski vs. snow/ice contacting forces once a skier or test pilot travels over it.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A force measurement apparatus configured to study reaction forces in a horizontal direction and a vertical direction between a first test object and a second test object, said force measurement apparatus comprising:
   a rigid top plate onto which said first test object is configured to be mounted or fixated;
   a rigid middle plate;
   a rigid base plate configured to be positioned on a rigid surface;
   a sliding member with a translational degree of freedom mechanically connecting said middle plate to one of said tip plate and said base plate, said sliding member is configured to allow said middle plate and said one of said top plate and said base plate to move relative to one another in a direction of said translational degree of freedom of said sliding member;
   a first load cell connected to said middle plate and to said one of said top plate and said base plate in such a way that a relative motion between said middle plate and said one of said top plate and said base plate in said translational degree of freedom of said sliding member is prevented, said first load cell is configured to register horizontal forces acting on said first test object when said second test object is brought to physically interact with said first test object, said horizontal forces are oriented in said direction of said translational degree of freedom of said sliding member, said first load cell is configured to output a first output signal representative of said horizontal forces; and
   a second load cell connected to said middle plate and the other of said top plate and said base plate, said second load cell is configured to register vertical forces in a vertical direction on said first test object when said second test object is brought to physically interact with said first test object, said second load cell is configured to output a second output signal representative of said vertical forces.

2. The force measurement apparatus according to claim 1, wherein
   said sliding member is configured to connect said top plate to said middle plate, said sliding member is configured to allow said top plate and said middle plate to move relative to one another in said direction of said translational degree of freedom of said sliding member;
   said first load cell is connected to said top plate and to said middle plate in such a way that a relative motion between said top plate and said middle plate in said translational degree of freedom of said sliding member is prevented; and
   said second load cell is connected to said base plate and said middle plate.

3. The force measurement apparatus according to 2, wherein a connection between said first load cell, said top plate and said middle plate comprises:
   a counter bore with a through-hole made in said top plate;
   a first screw positioned in said counter bore and said through-hole made in said top plate;
   a first hollow spacer positioned around a portion of said first screw protruding from underneath said top plate;
   a first ball and socket joint connected via a thread and threaded rod to a first side of said first load cell, said first ball and socket joint is positioned around a portion of said first screw where said first hollow spacer ends;
   a bolt connecting said first ball and socket joint, said first hollow spacer and said first screw;
   a second ball and socket joint connected via a thread and threaded rod to the other side of the first load cell;
   a second hollow spacer positioned in between said second ball and socket joint and said middle plate; and
   a second screw inserted in a threaded hole in said middle plate joining together said second ball and socket joint and said second hollow spacer.

4. The force measurement apparatus according to claim 2, wherein said top plate comprises counter bores with through-holes into which screws are inserted to connect said top plate to said sliding member, said middle plate comprises threaded holes into which screws are inserted to connect said middle plate to said sliding member.

5. The force measurement apparatus according to 1, wherein said sliding member comprises a linear ball slide.

6. The force measurement apparatus according to 1, further comprising an analog to digital converter connected to said first load cell and said second load cell.

7. The force measurement apparatus according to 6, wherein said analog to digital converter is powered by a low voltage output from a computer.

8. The force measurement apparatus according to 6, wherein said analog to digital converter is configured to provide an excitation voltage to said first load cell and said second load cell.

9. The force measurement apparatus according to 6, wherein said analog to digital converter is configured to convert said first output signal to a first digital output signal and said second output signal to a second digital output signal and to forward said first digital output signal and said second output signal to a computer configured to present said first digital output signal and said second digital output signal in real time and/or to store said first digital output signal and said second digital output signal to a file in a computer program run by said computer.

10. The force measurement apparatus according to 9, wherein said computer program run on said computer is configured to process said first digital output signal to compensate for an internal coefficient of friction in said sliding member in said horizontal force represented by said first digital output signal.

11. The force measurement apparatus according to 1, further comprising an external display comprising LCD and/or LED dot matrix display, said external display is connected to said first load cell and to said second load cell.

12. The force measurement apparatus according to 1, further comprising a ground cable connected to a metallic part of said force measurement apparatus.

13. The force measurement apparatus according to 1, wherein said first load cell is a s-type load cell and said second load cell is a single point load cell.

14. The force measurement apparatus according to 1, wherein said second test object is a hand held test object.

15. The force measurement apparatus according to 1, wherein said second test object is a media comprising a liquid and/or a gas.

16. The force measurement apparatus according to 1, wherein said force measurement apparatus is portable.

17. The force measurement apparatus according to 1, wherein said sliding member has two translational degrees of freedom.

18. The force measurement apparatus according to 17, further comprising a third load cell connected to said top plate and to said middle plate in such a way that in a second translational degree of freedom of said sliding member is prohibited, said third load cell is configured to register horizontal forces acting on said first test object when said second test object is brought to physically interact with said first test object, said horizontal forces registered by said third load cells are oriented in a direction of said second translational degree of freedom of said sliding member.

19. The force measurement apparatus according to claim 1, wherein said second load cell is configured to register said vertical forces regardless of where said vertical forces are acting on said first test object.

20. A method to study reaction forces between a first test object and a second test object, said method comprising:
   fixating said first test object to a rigid top plate of a force measurement apparatus configured to study reaction forces in a horizontal direction and a vertical direction between said first test object and said second test object, said force measurement apparatus comprising:
      said rigid top plate onto which said first test object is configured to be mounted or fixated;
      a rigid middle plate;
      a rigid base plate configured to be positioned on a rigid surface;
      a sliding member with a translational degree of freedom mechanically connecting said middle plate to one of said tip plate and said base plate, said sliding member is configured to allow said middle plate and said one of said top plate and said base plate to move relative to one another in a direction of said translational degree of freedom of said sliding member;
      a first load cell connected to said middle plate and to said one of said top plate and said base plate in such a way that a relative motion between said middle plate and said one of said top plate and said base plate in said translational degree of freedom of said sliding member is prevented, said first load cell is configured to register horizontal forces acting on said first test object when said second test object is brought to physically interact with said first test object, said horizontal forces are oriented in said direction of said translational degree of freedom of said sliding member; and
      a second load cell connected to said middle plate and the other of said top plate and said base plate, said second load cell is configured to register vertical forces in a vertical direction on said first test object when said second test object is brought to physically interact with said first test object;
   bringing said second test object to physically interact with said first test object;
   registering horizontal forces acting on said first test object by said first load cell of said force measurement apparatus;
   generating a first output signal representative of said horizontal forces acting on said first test object by said first load cell;
   registering vertical forces acting on said first test object by said second load cell of said force measurement apparatus; and
   generating a second output signal representative of said vertical forces acting on said first test object by said second load cell.

* * * * *